United States Patent [19]

Blake, III et al.

[11] Patent Number: 4,664,305
[45] Date of Patent: * May 12, 1987

[54] SURGICAL STAPLER

[76] Inventors: Joseph W. Blake, III, 88 Main St., New Canaan, Conn. 06840; Jack W. Kaufman, 357 Frankel Bvld., Merrick, N.Y. 11566

[*] Notice: The portion of the term of this patent subsequent to Jun. 18, 2002 has been disclaimed.

[21] Appl. No.: 691,071

[22] Filed: Jan. 14, 1985

Related U.S. Application Data

[63] Continuation of Ser. No. 374,692, May 4, 1982, Pat. No. 4,523,707.

[51] Int. Cl.⁴ .............................................. A61B 17/04
[52] U.S. Cl. ..................................... 227/19; 227/121; 227/DIG. 1
[58] Field of Search .................. 128/334 R, 334 L; 227/19, 109, 120, 121, 152, DIG. 1

[56] References Cited

U.S. PATENT DOCUMENTS

| | | |
|---|---|---|
| 1,674,437 | 6/1928 | Hubbard . |
| 1,744,700 | 1/1930 | Hubbard et al. . |
| 2,231,539 | 2/1941 | Larsen . |
| 2,240,455 | 4/1941 | Carlile . |
| 3,638,847 | 2/1972 | Noiles et al. . |
| 3,873,016 | 3/1975 | Fishbein . |
| 4,043,504 | 8/1977 | Hueil et al. . |
| 4,127,227 | 11/1978 | Green . |
| 4,166,466 | 9/1979 | Jarvik . |
| 4,179,057 | 12/1979 | Becht et al. . |
| 4,180,196 | 12/1979 | Hueil et al. . |
| 4,185,762 | 1/1980 | Froehlich ............... 227/19 X |
| 4,196,836 | 4/1980 | Becht . |
| 4,202,480 | 5/1980 | Annett . |
| 4,204,623 | 5/1980 | Green . |
| 4,406,392 | 9/1983 | Campbell et al. . |
| 4,410,125 | 10/1983 | Nolles et al. . |
| 4,427,008 | 1/1984 | Transue . |
| 4,448,194 | 5/1984 | DiGiovanni et al. . |
| 4,500,024 | 2/1985 | DiGiovanni et al. ............ 227/19 |

FOREIGN PATENT DOCUMENTS 711115 10/1941 Fed. Rep. of Germany .
WO82/00968 of 0000 PCT Int'l Appl. .

Primary Examiner—Paul A. Bell
Attorney, Agent, or Firm—Lackenbach, Siegel, Marzullo & Aronson

[57] ABSTRACT

A skin stapler having a plurality of staples comprising a frame structure, with a nose section for directing the staple at a wound site, including a housing therein having an anvil, a staple ejector, a driver for deforming the staple about the anvil, and a staple follower for continually urging the staples against a release member. Means are also provided for actuating the driver in a substantially translatable direction; and the actuating means comprises a toggle mechanism. In addition, the stapler is provided with means for restoring the driver to its unactivated position, and means are provided for preventing the double loading of the staples in said surgical stapler. The skin stapler is lightweight and of the disposable type as it is generally small and relatively compact.

9 Claims, 39 Drawing Figures

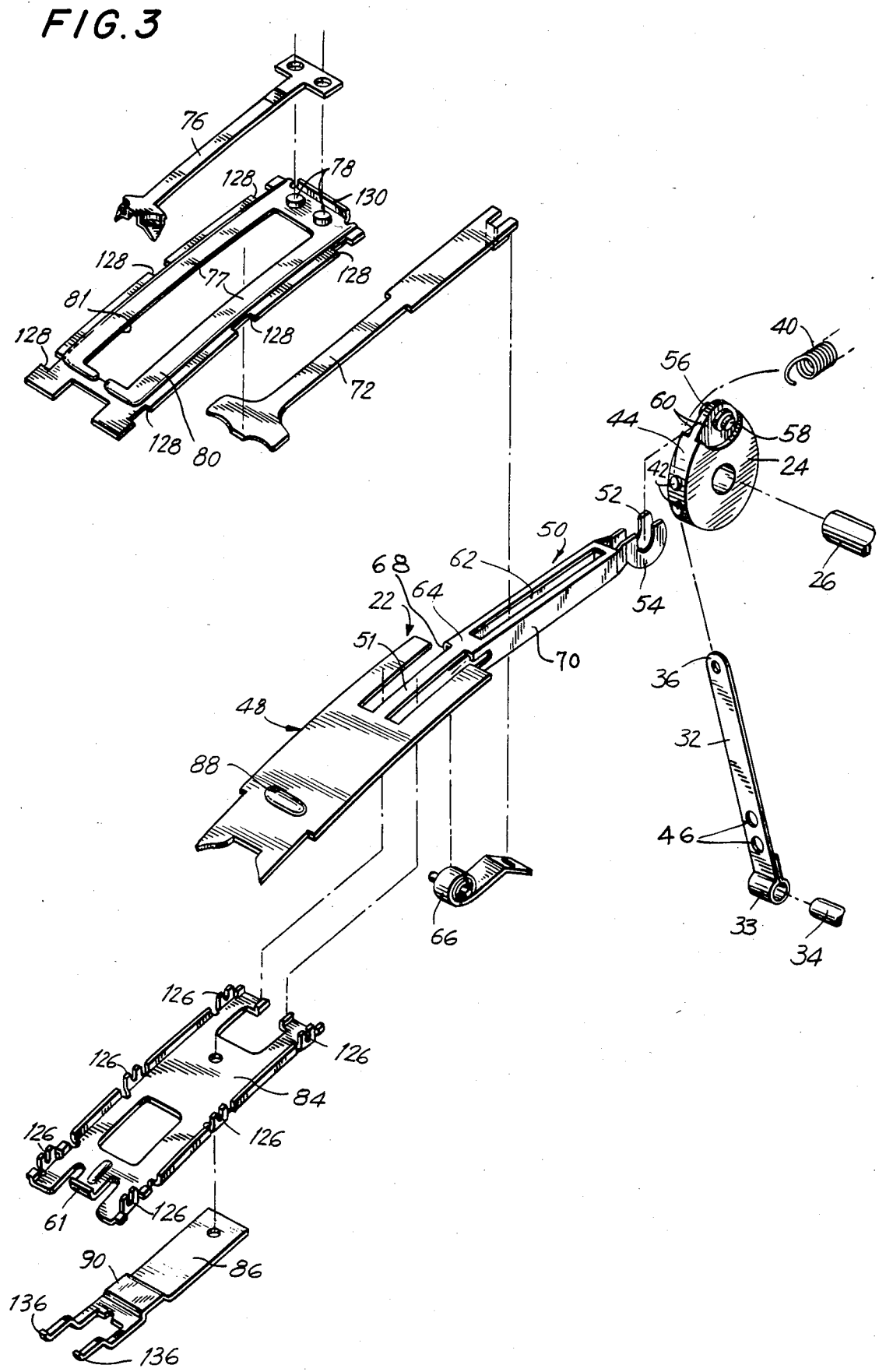

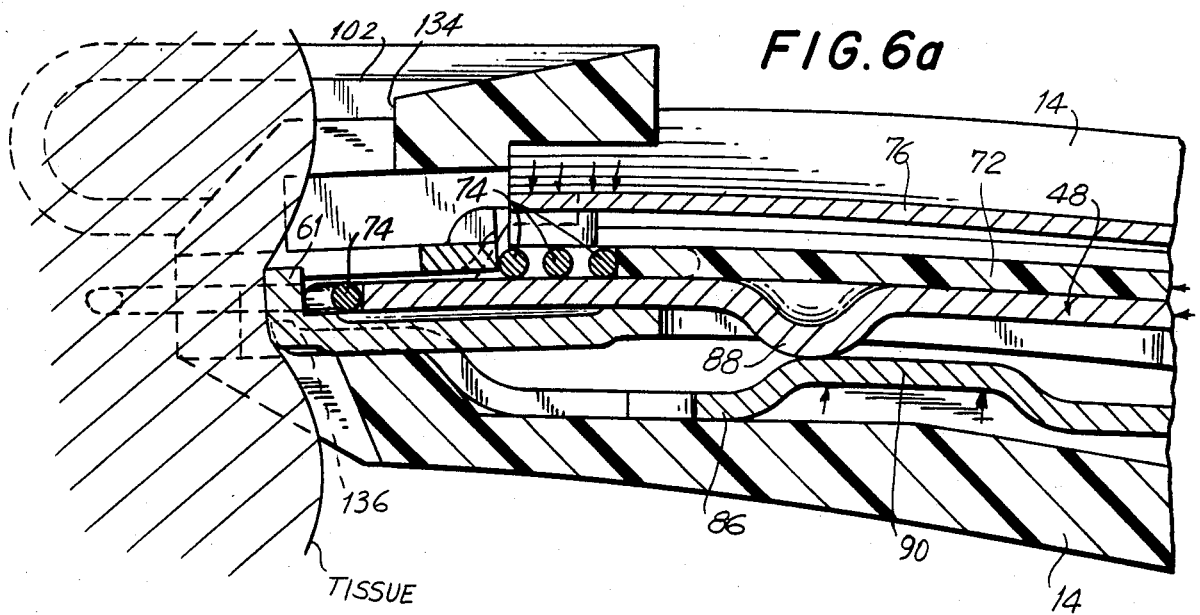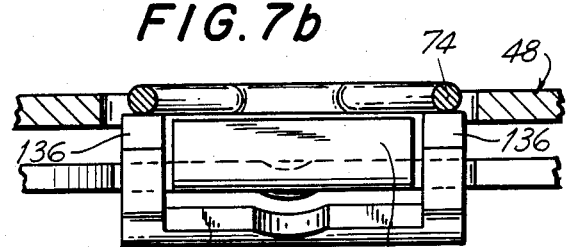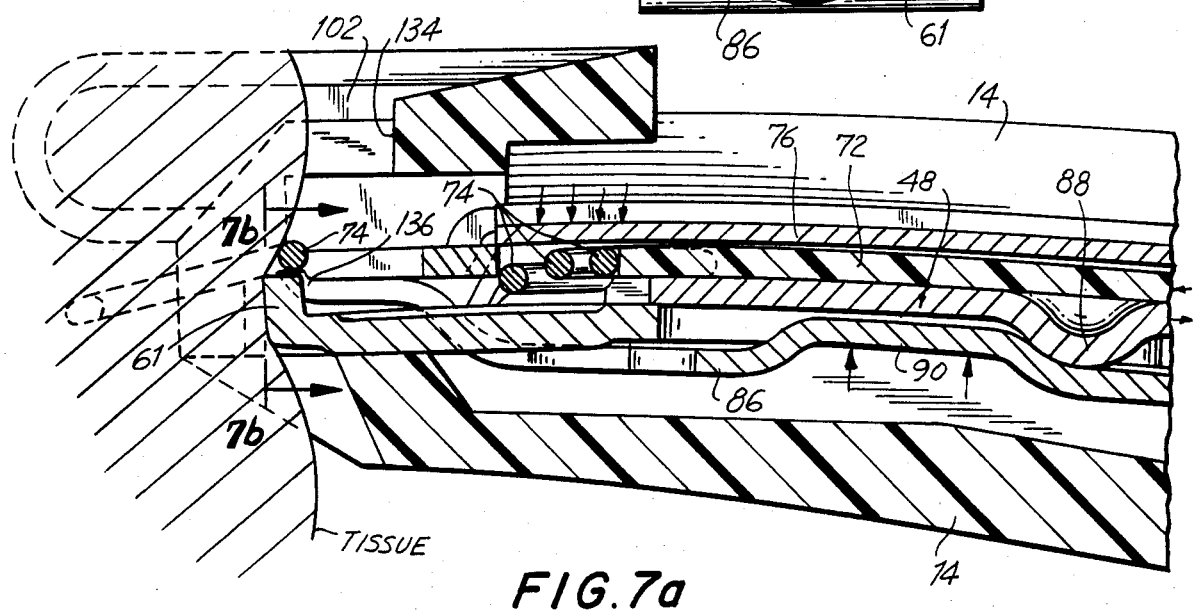

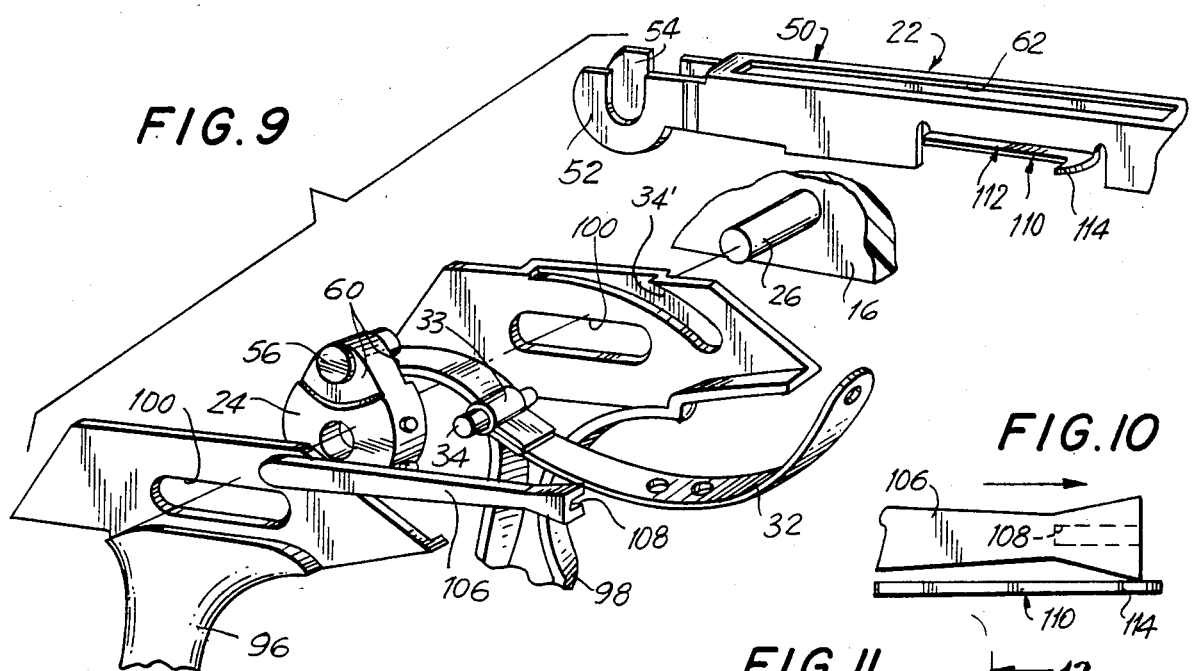
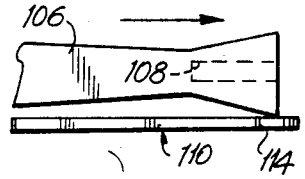
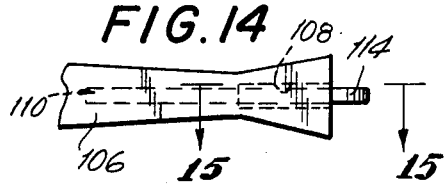
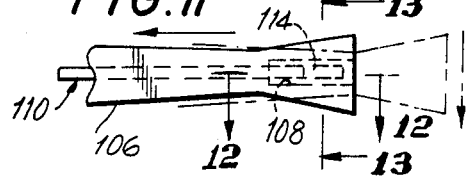
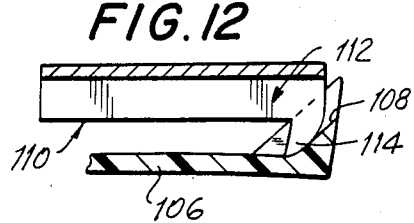
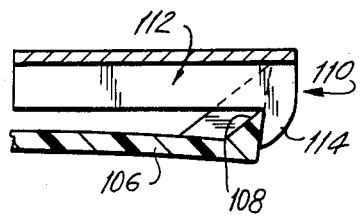
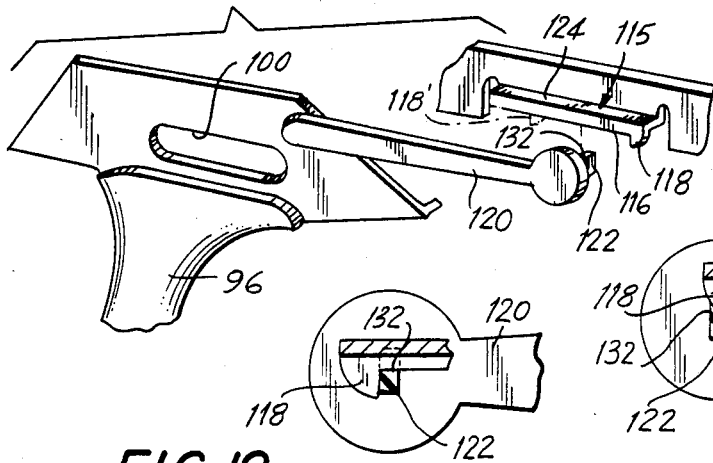
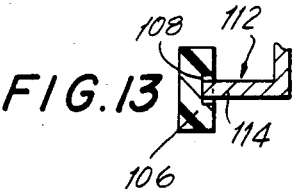
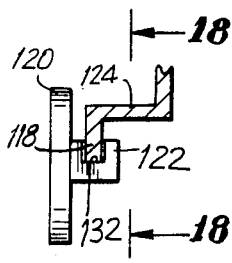

SURGICAL STAPLER

This is a continuation of application Ser. No. 374,692, filed May 4, 1982 now U.S. Pat. No. 4,523,707.

BACKGROUND OF THE INVENTION

This invention relates to improved stapling instruments, and more particularly to a surgical skin stapler which may be disposable after a single-use or application.

Modern medical procedures and equipment have led to significant advances in medicine, and there have been many new developments in recent years which have substantially contributed to better health care. One of such developments is the use of a skin stapler and metal staples to close a wound or incision, rather than the more conventional thread sutures for closing incisions in living tissue such as fascia or skin of a patient. Such use of skin staplers and metal staplers have clearly demonstrated a reduction in suturing time and thus overall operating time the patient must remain in the operating room under anaesthesia. The various stapling instruments developed and marketed heretofore in the medical profession comprise diverse constructions, such as manual and gas powered instruments, but none are yet widely accepted by all doctors for a number of reasons, such as poor visibility of wound site, cost, reliability, bulkiness, lack of familiarity with the product, clumsiness and/or difficulty in use, mechanical complexity, etc. Other surgical stapling instruments incorporate replaceable staple cartridges which may be changed when all of the staples in a single cartridge are utilized.

For example, U.S. Pat. No. 3,643,851 teaches a skin stapler with a staple cartridge and a trigger activated, gas-powered unit for driving a pusher forward to form the staple about an anvil and to eject same prior to returning automatically to its initial rearward position in the stapler ready for the next stapling cycle or sequences. Such instruments incorporating gas-powered driving means, however, do not lend themselves to wide acceptance as they must use sterilized gas, and must be periodically recharged with fresh pressurized gas cartridges or cylinders and such a maintenance requirement is simply disruptive to a doctor or surgeon. However, disposable gas powered staplers are now currently in use, but they, like any gas powered staplers, do not provide the doctor or surgeon with tactile feedback, unlike manually operated instruments which provide more flexibility in control and feel of staple bending and wound approximation. These gas powered staplers are also expensive and complex in operation.

In another medical stapler disclosed in U.S. Pat. No. 4,109,844, a spring-loaded means constantly urges and advances the staples along an anvil plate independent of the staple driver and the driving mechanism which actuates it. Also, a safety latch means to preclude inadvertent operation of the stapling instrument is provided in the stapler. Nevertheless, even though it employs a rotatable nose portion, its overall configuration, hand grip and vertical orientation to the wound site obstructs one's visability of the work area.

In U.S. Pat. No. 4,043,504, staples are stacked in a track of a removable and/or disposable cartridge and moved by spring means toward an anvil on the stapler. Each staple is shifted from a staple feeding track in the cartridge through a specifically sized window by means of a shifter closing the window to a separately divided staple forming track in the forming chamber which contains a former or driver. This unit further employs plural drive means for the staple feed and staple former and is otherwise complex in construction. In addition, the drive means are oriented perpendicular to the two tracks which have a divider wall therebetween and consequently its mechanical operation is achieved with difficulty and requires considerable space creating a more bulky stapler structure. In this regard, the cartridge of U.S. Pat. No. 4,043,504 is specifically intended to be used with the surgical stapling instrument disclosed in U.S. Pat. No. 4,196,836. This instrument has a handle portion and a straight nose portion rotatively mounted in the handle portion. The nose portion carries the instrument anvil and releasably supports the surgical staple carrying cartridge by means of a resilient latch configured to releasably engage the upper end of the cartridge in such a way as to urge the cartridge into abutment with both the nose portion and the instrument anvil.

U.S. Pat. Nos. 3,819,100, 3,949,924 and the disposable skin stapler covered by U.S. Pat. No. 4,204,623 (identified by the "Auto Suture" registered trademark of U.S. Surgical Corporation) all relate to manually-powered surgical stapling instruments and a staple-carrying cartridge, with a nose portion which is rotatably mounted in a hand-held main body portion so that the stapling angle can be varied without rotating the hand-held position of the stapler. Clutch means are also provided to ensure the staple-advancing drive means is only activated once per stapling operation. One of the disadvantages of the Auto Suture stapler is that its trigger is difficult to pull and it can inadvertently pinch flesh, fingers and linen or other items between the trigger and handle in certain positions of use.

A further medical stapling device is disclosed in U.S. Pat. No. 4,185,762. This device teaches a relatively simple structure wherein staples are moved along a track between grooved rails by a drive member having spaced lugs which are moved into engagement with the staples for advancing them along the track and simultaneously forming a first staple about an anvil. Rearward movement disengages the lugs away from the track so as to position the driver and it lugs for its next stapling cycle or sequence of continued operation.

U.S. Pat. No. 4,202,480 deals with a medical stapler provided with a device which leaves the ram across the staple in the opening to prevent another staple from being fed (double feeding) into the channel if manual activation of the stapler is discontinued before staple ejection. Also the stapler includes means for producing a "click" when the driver ram is moved fully to its eject position to provide both a tactile and an audible indication of the closing of a staple around the anvil.

Another U.S. Pat. No. 4,256,251 teaches a surgical stapler having a magazine or cartridge of staples secured to a base by spring clips and a pair of toggle-joint linkage handles which serve to drive a staple forming ram and bend a staple around the anvile. When pressure on the handles is released slightly, the anvil then is slid out from under the top of the staple.

Other skin staple cartridges such as U.S. Pat. No. 4,127,227 employ a stable cartridge embodying a belt system carrying a plurality of staples and ramp means for singly moving the staples out of the belt and into the plane of the pusher. In the surgical stapler of U.S. Pat. No. 3,873,016, the staple is pushed from the magazine into the driver chamber where it is engaged by the driver and pushed down the chamber to the anvil where it is deformed. Such a stapler also includes ratchet means for preventing a second staple from being fed into the guide while the one ahead of it is still being formed and yet to be ejected.

It is, therefore, a principle object of the invention to provide a unique and novel medical stapler for stapling skin or fascia.

Another object of the invention is to provide an entirely new stapler design which improves visibility at the suture or wound site, and control in the positioning or staple placement. A further object of the invention is to provide an improved skin stapler which has a slender, curved nose section and a closed handle and trigger portion, which are designed to function in an idealized manner with the human hand when in a clasped condition as in the case when pulling the trigger.

Yet another object of the invention is to provide a further improved skin stapler incorporating a driving mechanism which exhibits high driving forces within a confined area, but yet the manual force required to activate and drive the mechanism is small and easily and comfortably handled.

A still further object of the invention is to provide a skin stapler of the disposable type and one which holds a sufficiently large number of stored staples so that in most routine applications where the staples are used, switching instruments when the staples are exhausted is kept to a minimum.

SUMMARY OF THE INVENTION

In accordance with the invention, the skin stapler comprises a frame structure, with a slightly curved, nose section for positioning the staples at a suture site, and adapted to be gripped by a hand, including a housing therein supporting an anvil, a stapler ejector, a driver for deforming said staple about said anvil, and a staple follower for continually urging the staples against a release member; and means for actuating said driver in a substantially translatable direction; said actuating means comprising a toggle mechanism and means for restoring said driver to its unactivated position; and means for preventing the double loading of said staples in said surgical stapler.

In accordance with the invention, the skin stapler also comprises an entirely disposable unit having a housing including an anvil, a staple ejector, a driver for deforming the staple about the anvil, a staple follower and a release member; the housing further including means for holding the skin stapler while moving the driver from its normal unactivated position to a forming position where a staple is formed about the anvil by means of the driver.

The invention further concerns a surgical stapler for suturing tissue with staples, comprising a frame structure adapted to be hand held, including means for feeding, deforming and ejecting a formed staple, and further means for activating said means; and an approximating blade, disposed at the tip of said stapler where said staples are ejected, for centering the stapler about the approximated sides of the wound to be sutured.

Also, in accordance with the invention, one embodiment of the surgical stapler which is adapted to be hand held has a visible staple supply in the frame structure; the frame structure further comprising an anvil and a housing structure having a single track therein for a driver-following unit. The follower is secured to the driver and is resiliently biased so as to continuously urge said plurality of staples which are stacked end to end atop the driver to a forwardly position. A release member is disposed above the most forward staple for urging a staple into position in front of the driver, with the driver being manually actuated by actuating means for traveling between a forming position for closing said staple about the anvil and a retracting position in said track for reloading a next staple in front of said driver. The driver upon retracting permits only a single staple to move independently of the actuating means into position in front of said driver without a direct actuation of the stapler.

Another form of skin stapler has stored therein a plurality of staples and has a frame structure, with a nose section for directing the staples at a suture site. The stapler is also adapted to be gripped by a hand, with the stapler housing supporting an anvil, and having a single track encompassing a driver for deforming said staple about the anvil and a staple follower is in juxtaposition to said driver for continuously urging said staples forwardly in the single track in cooperative association with a release member. Further, the staple is provided with manually operated actuating means for actuating the driver in a substantially translatable direction by a toggle-like drive mechanism for forming a closed staple about said anvil biasing means restores the driver to its unactuated position; and the staples are stacked and nested end to end between the driver and the upper portion of the housing. Thus, when the driver is to be restored to its unactuated position by the biasing means, a single staple from the front of the stack of staples is urged and moves into position in front of the driver so as to be formed about said anvil upon the driver being actuated.

The invention also encompasses a surgical staple for joining the severed skin or facia of a body comprising, prior to emplace ment, a curved central portion, straight portions extending upwardly and outwardly from opposite ends of said curved central portion, straight portions extending upwardly and outwardly from opposite ends of said curved central portion at obtuse angles, and straight portions extending downwardly and outwardly from curved portions connecting said upwardly and outwardly straight extending portions with said downwardly and outwardly straight extending portions, and said straight portions being about equal in length to each other.

BRIEF DESCRIPTION OF THE DRAWINGS

The present invention will be further described with reference to the accompanying drawings wherein like reference numerals refer to like parts in the various views, and wherein:

FIG. 3 is an exploded, perspective view of the innards of the stapler, including the actuating drum and staple driving mechanism;

FIG. 5 is a view similar to that of FIG. 4, but with the top cover and escapement spring of the staple driving, mechanism removed, and with the follower and row of staples illustrated and generally illustrating a forward moving position with a single staple having been advanced and wedged between the driver and the anvil;

FIG. 6 is a further view like that of FIGS. 4 and 5, but with the follower and row of staplers removed, and generally illustrating a complete crimping and stapling position;

FIG. 6a is a further enlarged, fragmentary cross-sectional view, taken along the line 6a—6a of FIG. 6;

FIG. 7 is another view like that of FIGS. 4–6, but with the driver removed, and illustrating the ejector having lifted the crimped staple off the anvil;

FIG. 7a is an enlarged, fragmentary cross-sectional view, taken along the line 7a—7a of FIG. 7;

FIG. 7b is a fragmentary cross-sectional view, taken along the line 7b—7b of FIG. 7a;

FIG. 9 is an exploded, perspective view of an anti-jam or "fail safe" ratchet mechanism which insures that only one staple is advanced through a complete sequence of staple closure operation once the cycle is commenced;

FIG. 10 is a fragmentary, side elevational view of the front end of a resilient follower or pawl-arm riding a camming surface of a ratchet;

FIG. 11 is a view similar to that of FIG. 10, but illustrating in phantom lines the front end of the follower riding over the caming surface and returning back with the tooth of the ratchet engaged in the slotted portion of the follower;

FIG. 12 is a cross-sectional view, taken along the lines 12—12 of FIG. 11;

FIG. 13 is a cross-sectional view, taken along the lines 13—13 of FIG. 11;

FIG. 14 is a view similar to that of FIG. 11, but illustrating the follower or pawl arm locked in a position of forward movement by the tooth having engaged the front edge of the follower;

FIG. 15 is a cross-sectional view, taken along the lines 15—15 of FIG. 14;

FIG. 16 illustrates in perspective an alternate modification of the anti-jam or "fail safe" ratchet mechanism shown in FIGS. 9–15;

FIG. 17 is a fragmentary end view, showing the tooth of the ratchet in the slotted portion of the follower projection;

FIG. 18 is a cross-sectional view, taken along the lines 18—18 of FIG. 17;

FIG. 19 is a view showing the follower locked in a position of forward movement by the tooth having engaged the front edge or surface of the follower projection;

DESCRIPTION OF THE EMBODIMENTS

Figure 1:
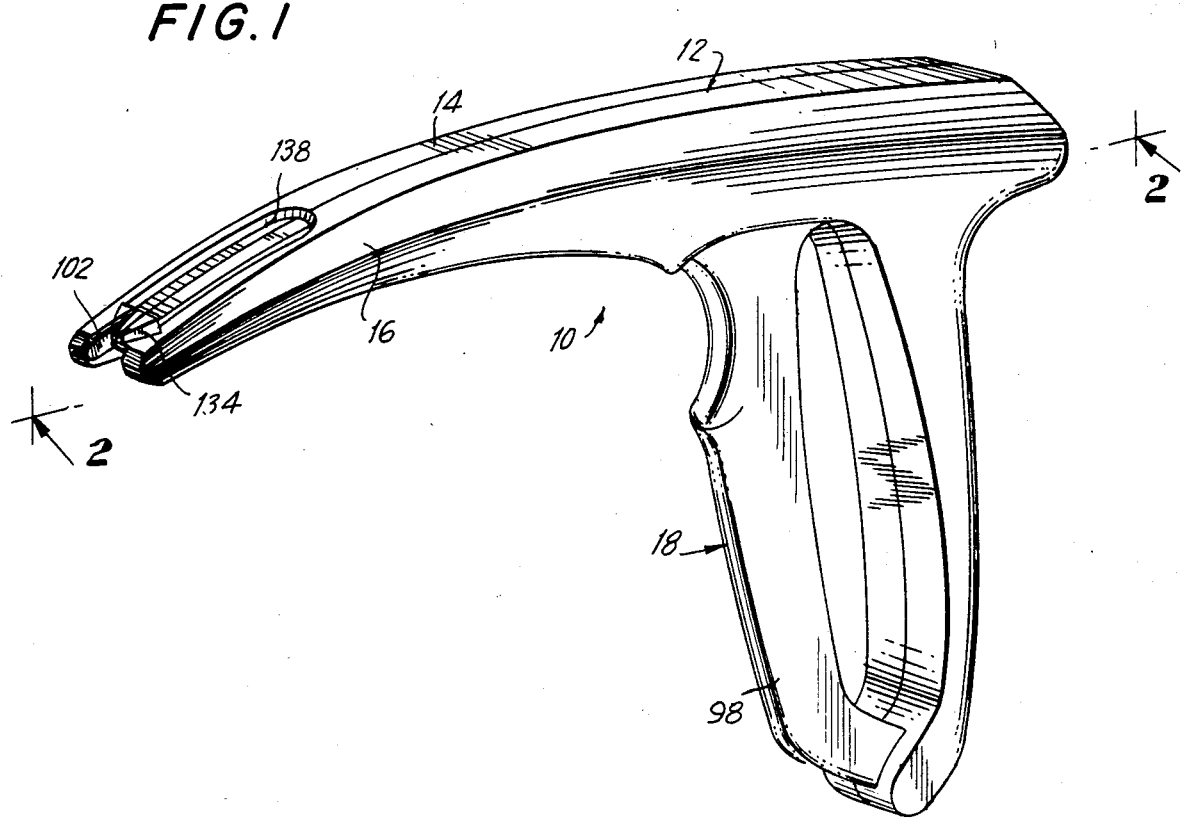
FIG. 1 is a front perspective view of a surgical stapler in accordance with the present invention.

Referring now to the drawings, and in particular to FIGS. 1–8, there is shown our novel medical surgical skin stapler generally designated by the reference numeral 10. The stapler 10 comprises a frame 12, preferably comprising paired halves 14 and 16 having a rearward portion defining a gripping element, and including a generally translatable trigger element 18, preferably of a length which forms a closed handle portion substantially orthogonal to the top upper portion 20 of the frame 12. The shape and grip is such as to be conveniently gripped with one hand of a surgeon.

Figure 2:
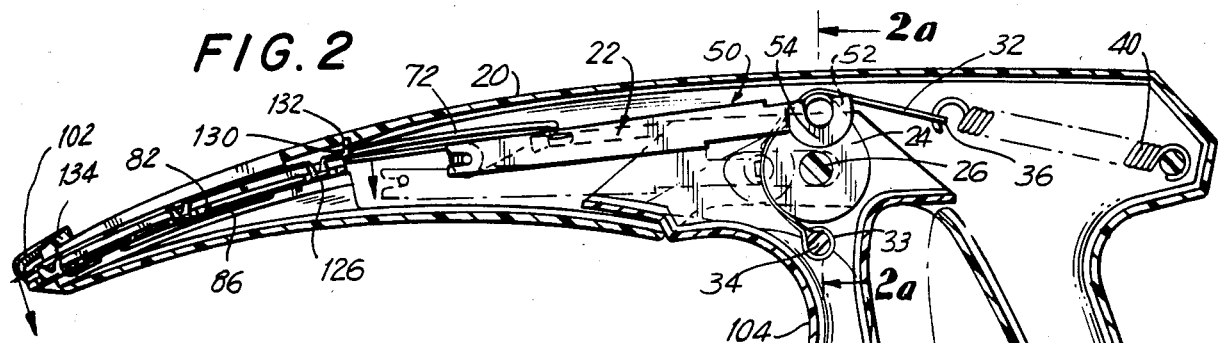
FIG. 2 is a cross-sectional view thereof, taken along the line 2—2 of FIG. 1.
Figure 2A:
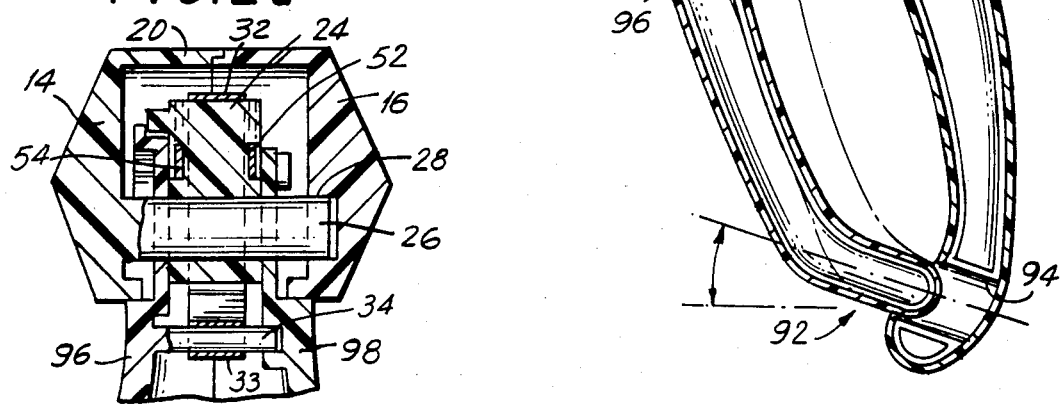
FIG. 2a is a fragmentary sectional view, taken along the line 2a—2a of FIG. 2.
Figure 4:
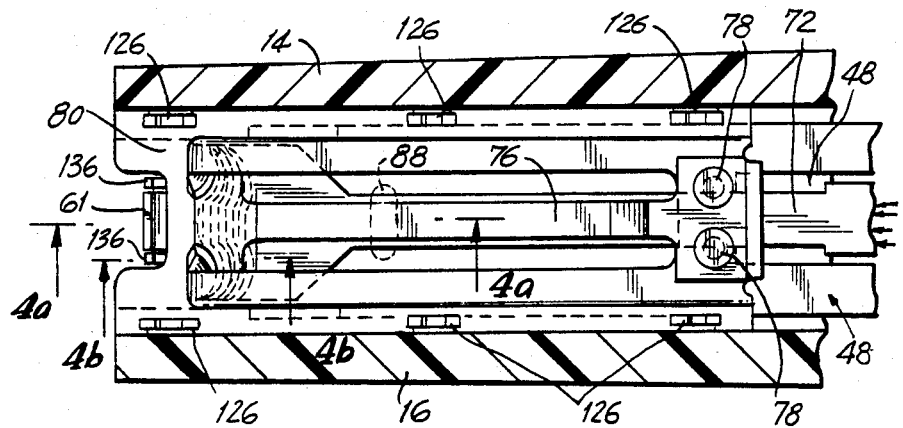
FIGS. 4–7 generally illustrate the operational sequence of staple closure, with FIG. 4 representing in a top plan view the front portion of the stapler with the split housing cut away to show detail, and generally illustrating a starting position.
Figure 5:
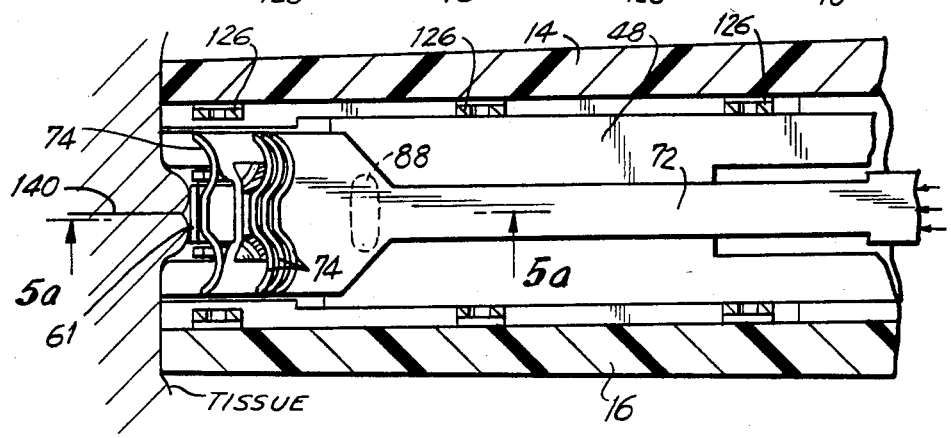
Figure 6:
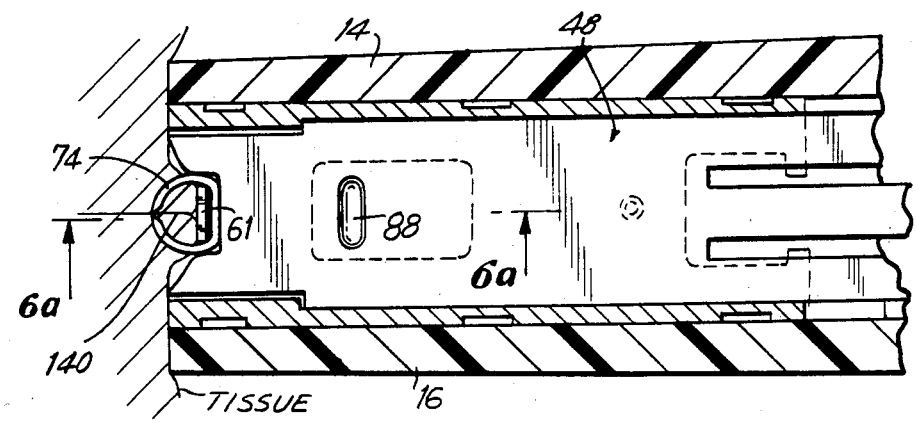

As best shown in FIGS. 2, 2a and 3, a pusher or driver 22 is moved or generally provided with translational motion by means of an actuating drum 24 supported on a shaft 26 extending from half 14 and said shaft 26 being in a suitable bearing support provided in the paired halves 14 and 16 of the frame 12. Wrapped about the actuating drum 24 is a resilient strap 32, preferably made of metal, such as stainless steel, anchored at one end, suitably by means of a closed loop 33 of the strap 32, to a pin 34, suitably affixed to the trigger element 18. The other end 36 of the strap 32 is connected to resilient means, such as the return extension spring 40, for continually tensioning and urging rearwardly the "return" of the strap 32, and in turn the drive 22 through the action of the actuating drum 24, as will be explained in greater detail hereinafter.

The actuating drum 24 is rotated about its shaft 26, as shown in phantom FIG. 2, when the trigger element 18 and strap 32 are pulled back by means of a pair of projections 42 (see FIG. 3), suitably provided on the drum's peripheral surface 44 and which project through a suitable pair of mating apertures 46 in the strap 32. The actuating drum 24 acts as a toggle mechanism in providing the necessary driving forces required to move the driver 22 and subsequently perform the forming and/or stapling operation for each staple used; with the driving forces acting tangentially to the peripheral surfaces 44 of the actuating drum 24.

As best shown in FIG. 3, the driver 22 comprises a front portion 48 and a rear channel shaped connecting portion 50, bendable and/or resilient in an intermediate flexible linking portion 51 as said intermediate portion 51 acts as a hinge between and transfers forces between said front and rear portions 48 and 50. The driver 22 is also preferably of one piece construction. The distal end of the rear connecting portion 50 is provided with suitable arcuate side elements 52 and 54 for connection to the actuating drum 24 about a pair of oppositely disposed lugs 56 and 58 formed by suitable recess means 60 cut into the side surfaces of the drum 24. Such toggle driving arrangement provides the necessary high forces required to form the staple about the anvil 61 which is located on the bottom cover 84.

Through means 62, such as, for example, the elongated slot in the top surface portion 64 of the channel shaped connecting portion 50 of the driver 22, a negator spring 66 is suitably mounted about a shaft to the parallel sides 68 and 70 of the channel driver 22 and to a follower 72, for maintaining a continuing force on the follower 72. Thus, a constant pressure on the row of staples is provided to urge them forward at all times. The follower 72 continually urges the row of staples 74 against the formed front underside of an escapement spring 76 which is in mutual cooperative association with an open unformed staple. The escapement spring 76 which is resilient also maintains a constant downward pressure for moving or shifting downwardly a single staple in front of the driver 22. The staples 74 are retained beneath the opposite edges 77 of the cover 80 in a single track 79 which also accommodates the follower 72 and driver 22.

Figure 7:
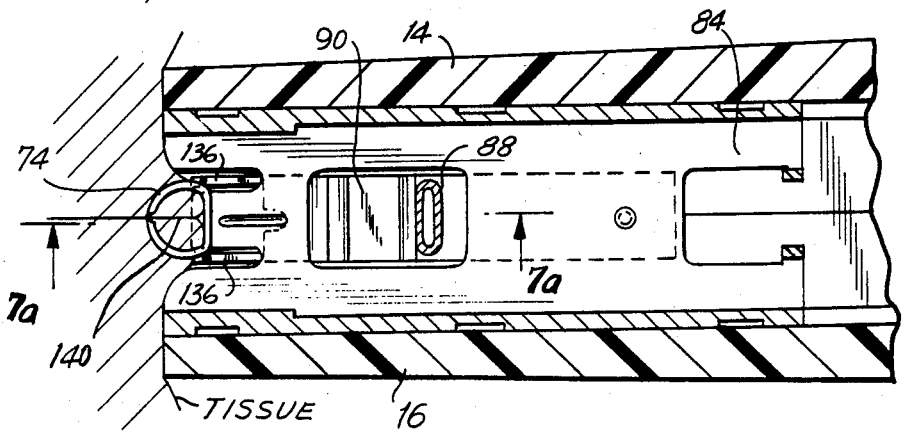
Figure 4A:
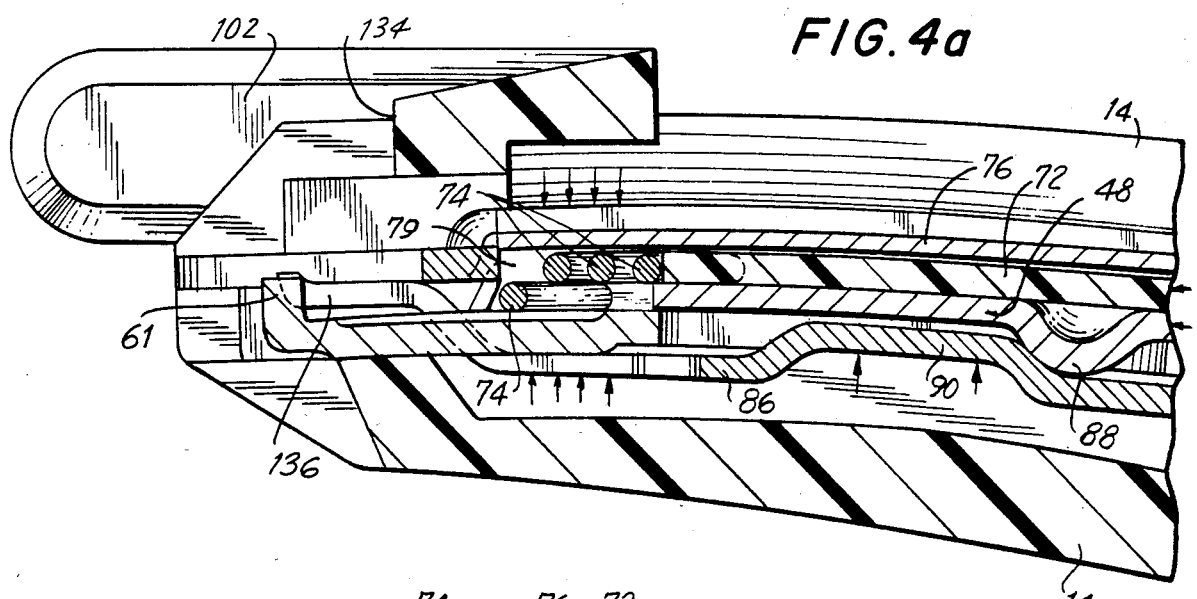
FIGS. 4a and 4b are enlarged, fragmentary cross-sectional view, taken, respectively, along the lines 4a—4a and 4b—4b of FIG. 4.
Figure 4B:
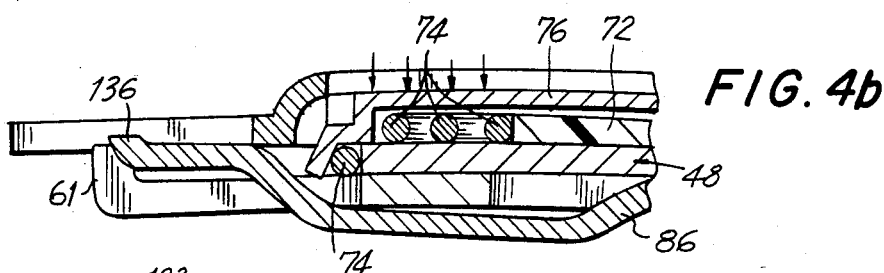
Figure 5A:
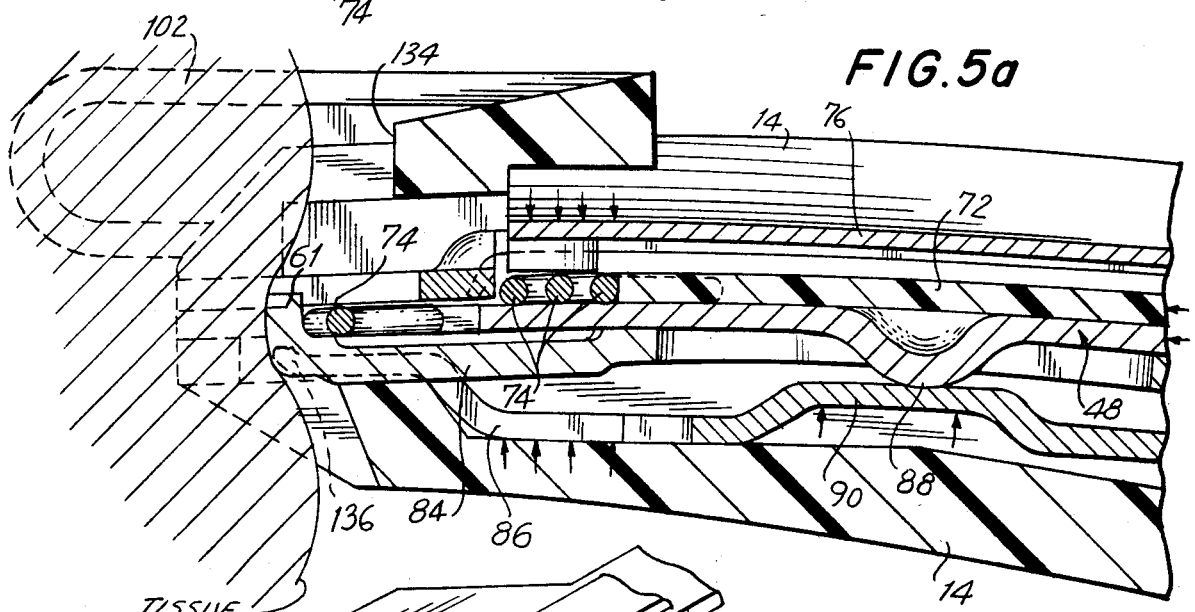
FIG. 5a is another enlarged, fragmentary cross-sectional view, taken along the lines 5a—5a of FIG. 5.
Figure 8:
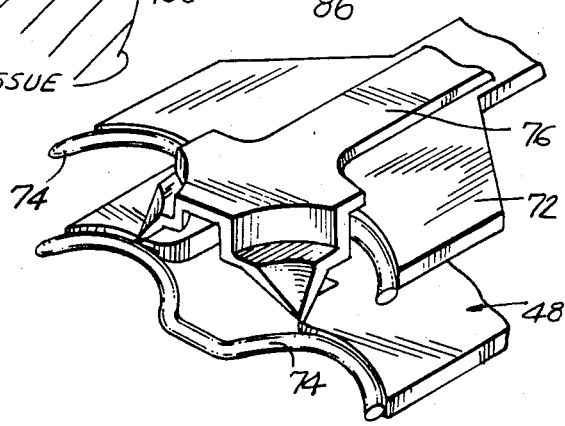
FIG. 8 is a greatly enlarged, front fragmentary view in perspective of a staple between the escapement spring and follower, and another staple in front of the conforming curved front edges of the driver.

The follower 72, since it should freely slide between the driver 22 and the top cover 80, is preferably made of a material exhibiting low frictional resistance, such as "Delrin", a trademark of the DuPont Company of Wilmington, Del. The escapement spring 76 is suitably secured, such as by welding, riveting or peened over pins 78, to the top cover 80. Secured in a like manner to a bottom cover 84 is a suitable ejector 86 which functions to eject a formed or closed staple 74 as is best shown in FIGS. 7a and 7b. Alternately, the escapement spring 76 may also be formed integrally with the top cover 80 and comprise a resilient cantilevered element stamped out from the central open cut-out area 81 in the top cover 80. The shifting movement up and down of the ejector 86 is governed by a depression or "elongated" dimple 88 in the driver 22 and a mutually cooperative raised portion 90 on the ejector 86. FIGS. 4a–7a clearly show the interaction and cooperative association between the dimple 88 of the driver 22 and the raised portion 90 of the ejector 86. Alternate means for ejecting and a modified escapement spring may be employed as will be discussed hereinafter.

The bottom end 92 of the trigger element 18 is guided for translational movement in a bore 94, preferably of the blind type (although a though hole is also satisfactory), with the bore being disposed at an angle of about 14° to about 24° with the horizontal. Preferably, an angle of about 19° is employed as with this angle, a most satisfactory balance of forces is achieved with the hand in an open to closed position as when the hand is gripping the stapler. This arrangement also ensures that as the staple is being formed and applied to a wound, the nose section of the stapler is maintained in a stationary manner and does not exhibit any "kicking up" action as do some of the prior art staplers, such as U.S. Surgical's. The movement of the bottom end 92 in the bore 94 is somewhat less than the movement of the upper end of the trigger element 18 relative to the actuating drum's shaft 26, as the path of travel at the upper end is longer. In this regard, the trigger element 18 also may comprise paired halves 96 and 98, each with a suitable slot 100 at their upper ends for guiding the trigger element 18 when actuated by pulling and for its return when released. In addition, the trigger element 18 may be provided with gripping means, such as at least one finger grip 104. The index finger as the trigger 18 is squeezed is relieved of the power required to actuate the trigger element 18 and it thus provides maximum or total control to the stapling operation. The nose section of the stapler being relatively thin (about $\frac{1}{8}$–174 inch) and being curved downwardly provides increased visibility at the wound site which is vitally important to the surgeon as proper placement of the staples is greatly facilitated. If desired, an approximating blade 102 which is mounted to (or held between) the housing maybe provided with a suitable scored line (not shown) so that it can be removed by breaking it off should a particular surgeon desire not to utilize such a centering device. It should also be appreciated that the closed trigger loop of our skin stapler, precludes catching or squeezing one's fingers, or flesh of the patient or snagging linen or other materials, etc. between the trigger and handle, which not only can cause considerable discomfort to a person, but also disturb the concentration of the doctor or surgeon during his suturing procedure.

Referring now to FIGS. 9–15, there is shown an anti-jamming or "fail safe" ratchet mechanism for preventing double loading, thus ensuring that once a cycle or sequence of staple placement is started, it must be finished to completion before a new staple can commence the next placement cycle or sequence. As shown therein, the mechanism comprises a resilient deflecting follower or pawl arm 106, having a notched area 108, which may be, if desired, integrally molded into one of the paired halves 96 and 98, and a ratchet 110, preferably integrally formed with the driver 22, having top or track-like surface 112 and a front tooth 114. Initially, the front of the pawl arm 106 resides in front of the tooth 114 and is not in contact therewith. As the handle is pulled back, the tooth 114 is engaged and part of the pawl glides on the lower surface as the trigger is pulled rearwardly. The pawl arm 106 is then deflected and stressed downwardly until the rearmost position of the trigger is reached. The pawl arm 106 then leaves the surface and pops to a stress-relieved position. When the trigger is released, the pawl arm comes down into contact with the top surface, and thereafter is deflected upwardly and stressed until the trigger reaches a full forward position. At this time, the pawl arm snaps back to its original non-contacting position ready for the next cycle. The pawl arm 106 is resilient and deflectable so that it generally rides on the camming surface 112 of the ratchet 110 until it is initially deflected downwardly and is locked behind the tooth 114 precluding its forward travel. This locked position of the pawl arm 106 and trigger element 18 to which it is connected occurs almost immediately after the trigger element 18 is initially pulled back to start a cycle for the placement of a staple.

The curved slot 34' provided on at least one of the handles, shown in 98 on FIG. 9 provides a tracking path for locking in position at any given point the strap 32 during the stroke or cycle of operation of the stapler so that the flexible strap 32 cannot be kinked since it is forced to travel along the fixed glide path.

In the modification of FIGS. 16–19, the ratchet 115 forms a downwardly extending cam track 116 with a front tooth 118 which is engagable with a pawl arm 120 having a channel-shaped projection 122 which rides on the cam track 116 as the trigger element 18 is pulled back (FIG. 17). As shown in FIGS. 18 and 19, the front tooth 118 prevents the pawl arm 120 from moving forward once the tooth 118 snaps behind the channel-shaped projection 122. On the trigger's return the pawl arm 120 rides on the top camming surface 124 of the ratchet 115. The operating cycle of this modification is essentially the same as that described hereinabove for the ratchet mechanism of FIGS. 9–15.

As shown in phantom in FIG. 16, a second tooth 118' may also be employed with both ratchet embodiments for precluding the trigger from inadvertently releasing the full retracted force into the front tooth 118 in the event the handle slips or the trigger is released unintentionally. Such a second tooth 118' would protect the pawl arm 120 of the half 96 from fracturing if the trigger was accidentally released in the fully retracted position as the second tooth 118' would stop the pawl arm and released trigger in its rearward positions and keep same from rushing forward into the first tooth 118. The second tooth is preferably placed in the pre-cocked position where the staple is just about ready to be formed about the anvil.

Figure 20:
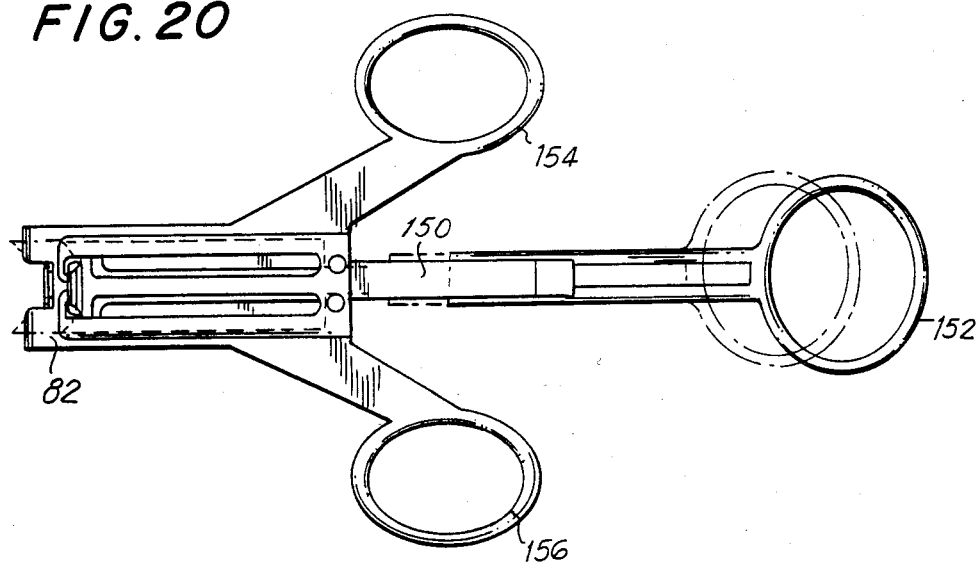
FIGS. 20–24 are diagramatic illustrations of just five alternate constructions of means for activating the driver so as to move the driver forward for expelling and forming a staple about said anvil, which incidentally does not require much force at all.

FIGS. 20–24 diagrammatically illustrate a few alternate forms of our disposable skin stapler. For example, as shown in FIG. 20, the driver 150 is provided with an extension in the form of a "thumb" finger loop 152 for actuation of the stapler as shown in phantom, and as is similarly done with a conventional type of syringe, wherein additional finger loops 154, 156 are provided on opposite sides of the body or housing 82 for holding purposes. The housing 82 further encompasses all of the other elements of the skin stapler, namely, the ejector, the bottom cover, follower, top cover and the escapement spring. Of course, with such a skin stapler, one must manually return or retract the driver 150 to its initial position shown in FIG. 20 as no return spring is employed. Such a stapler may be of the "single shot" type or it may be provided with a plurality of staples just like the embodiment of FIGS. 1–8. However, a compression spring may be employed between the finger loop 152 and the housing 82 so as to return the driver 150 to its unactivated position.

Figure 21:
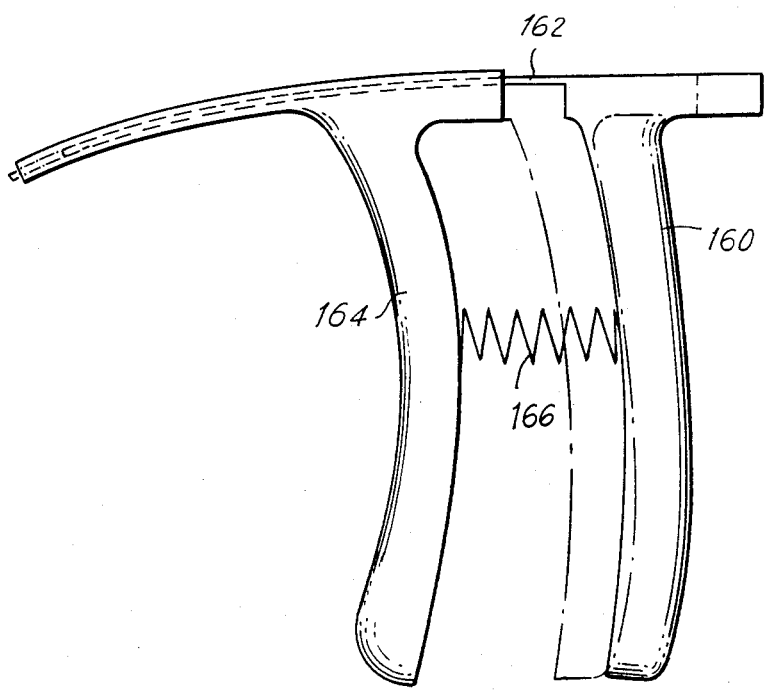

FIG. 21 illustrates another alternate form of our stapler in side elevation, wherein an extension 160 of the driver 162 is in the form of a sliding handle and a fixed trigger element 164 forms part of and or extends from the body or housing 82. In this embodiment of the invention, a return spring 166 may be employed between the handle 160 and trigger 164 for returning the handle to its normal position.

Figure 22:
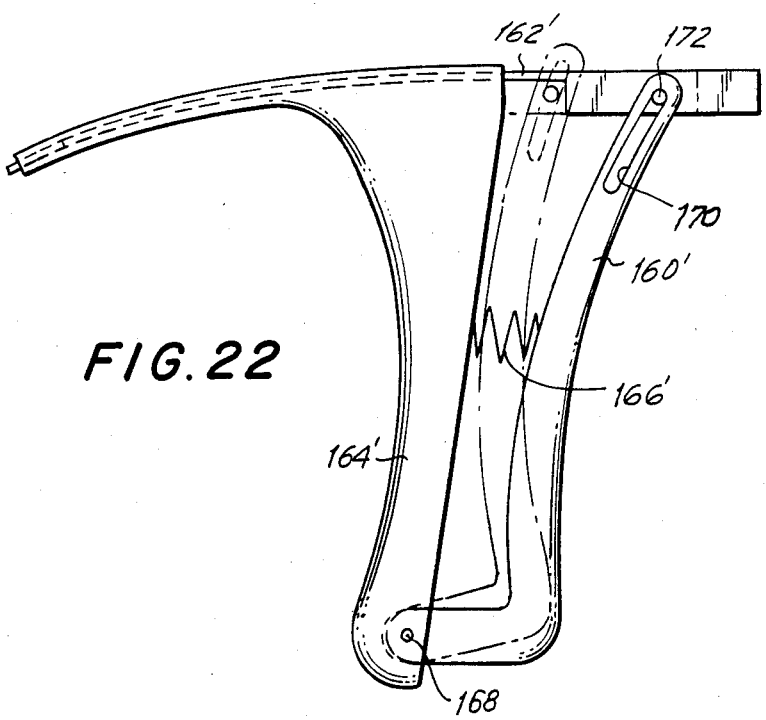

The embodiment of FIG. 22 is similar to that of FIG. 21, but employs a pivoting type of handle 160' pivoted at 168 and is provided with a slot 170 for engagement with a pin 172 provided on the driver 162'. This skin stapler operates in essentially the same manner as that of FIG. 21, but it has a "closed" handle portion in lieu of an open handle portion.

Figure 23:
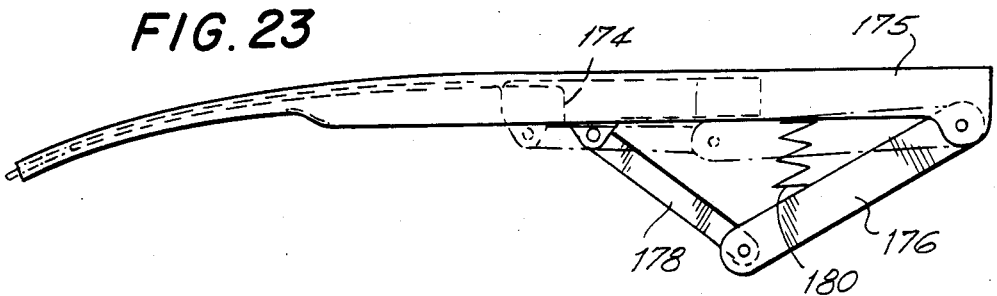

FIG. 23 further illustrates a very compact form of stapler wherein handle means in the form of a pair of connecting pivotable or toggle links when actuated provide together the driving force for the driver 174. In this example, the handle link 176 is attached to an extension 175 of the housing 82 and is squeezed for moving the driver 174 forward by means of an intermediate link 178. Spring 180 returns the links to their normal position as shown by the solid lines.

Figure 24:
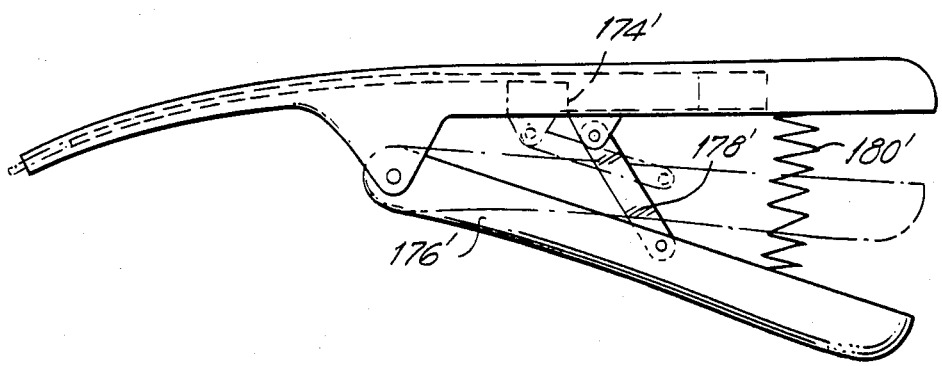
Figure 25:
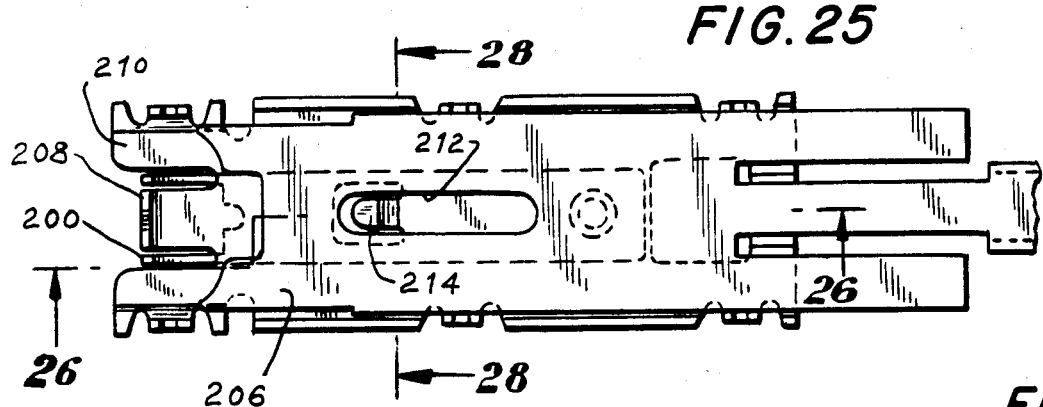
FIG. 25 is a top plan view of a bottom housing cover with an alternate construction embodying a modified ejector spring and driver.

FIG. 24 is similar to FIG. 23, except that here the handle link 176' is pivoted and attached up front to the housing 82, with the intermediate link 178' and spring 180' in generally the same positions.

Figure 26:
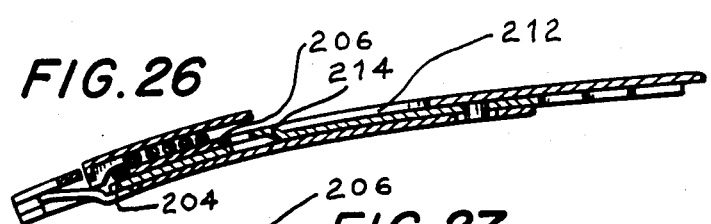
FIG. 26 is a longitudinal sectional view taken along the line 26—26 of FIG. 25; and showing escapement spring and staples.
Figure 29:
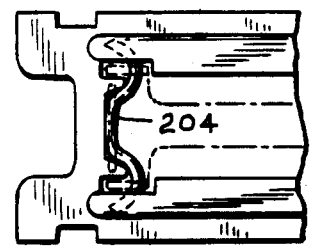
FIG. 29 is a fragmentary top plan view of the cover housing and escapement spring (shown in phantom) employed with the alternate construction shown in FIGS. 25–28.
Figure 27:
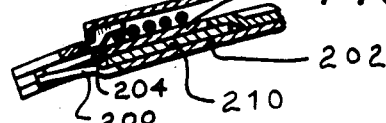
FIG. 27 is a fragmentary sectional view, similar to that of FIG. 26, but showing advanced driver and raised escapement spring.
Figure 30:
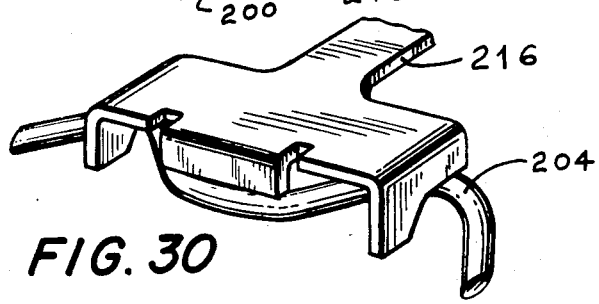
FIG. 30 is a fragmentary perspective view of the escapement spring shown in its engagement with a staple.
Figure 28:
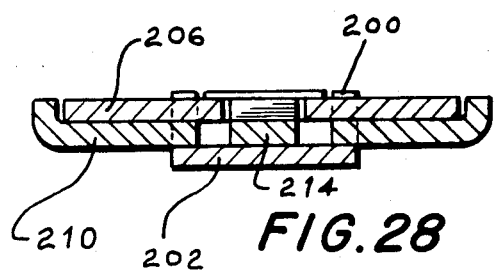
FIG. 28 is a transverse sectional view taken along the line 28—28 of FIG. 25.

FIGS. 25–30 show a preferred construction of the stapler mechanism of the apparatus of the invention. Here, the leading edges of the forward or first staple pushes down the paired tangs or legs 200 extending from the end of ejector 202 as the staple 204 advances forward to be formed about an anvil 208. Thus, when the driver 206 is retracted, the legs 200 immediately push up the staple 204 and advance it off the anvil 208. Constant pressure is therefore maintained on the staple 204 as it is moved to the front of the stapler. The legs or tangs are inclined slightly upwardly about 10° to further aid in keeping the staple 204 in position and precluding it from dropping forward or falling loose at the front of the stapler. Other preferred features of the invention are accurate alignment means between driver 206 and bottom cover 210, and the three point staple contact maintained by escapement spring 216 (FIG. 30). As best shown in FIGS. 26–28, the driver 206 is suitably provided with groove means 212 which cooperates with pin means 214 in the bottom cover 210. With such disposed pin and groove means or vice-versa, the staple is precisely aligned or centered about the anvil even though the width of the single track is slightly larger than the width of the staples to allow for clearance. This alignment feature between driver and bottom cover, as well as the modified ejector and escapement spring or release member 216 are interchangeable with and may be substituted in lieu of the ejector 86, driver 48, bottom spring 76, and top and bottom covers of the embodiment of FIGS. 1–8. The escapement spring 216 has a delayed raising action (see FIG. 27) due to the driver 206 moving a greater forward distance before urging the spring up. This action ensures that only one staple is acted on at any one time by the driver.

Figure 31:
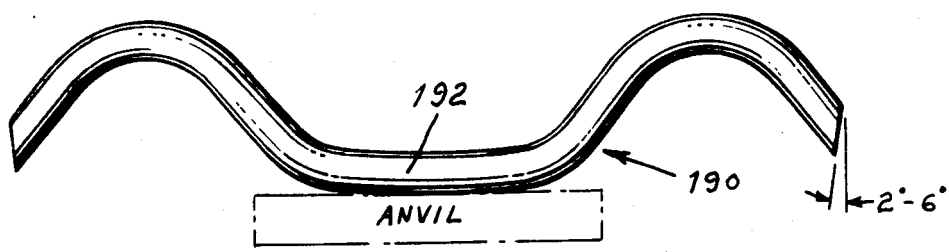
FIG. 31 is a plan view, of a staple designed for used with the skin stapler, with the staple shown in the undeformed state with reference to the anvil about which the staple is formed.
Figure 32:
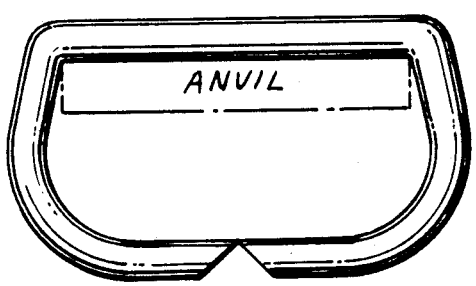
FIG. 32 is another plan view, of the staple of FIG. 31, but showing the staple formed about the anvil.

The staple most suitable for use with the stapler of the invention, although any staple of similar size and shape would also suffice so long as driver and follower profiles conform to the staple profile, is best shown in FIGS. 31 and 32. As shown therein, the staple 190 comprises seven portions, a curved central portion 192 smaller than the width of the anvil, and on opposite sides thereof short upwardly and outwardly portions as well as short downwardly and outwardly portions, all of the same length, connected together by curved portions. With such a construction, the staple enters and leaves the suture site with minimum trauma as the ends of the staple track the same path generally in each operation; and the retention power of the staple is more than satisfactory for its purpose. The diameter or wire size of the staple may be of any suitable size, such as, for example, 0.0225" or 0.021" and may be fabricated from a suitable stainless steel, with as reference anvil width of 0.230 inch for the heavier staple and 0.173 inch for the lighter staple. Such staples provide a generally closed box-like configuration when fully formed about the anvil with their sharp pointed tips just about "kissing" each other when the staple is closed, to form a parallelogram structure, as shown in FIG. 32. Other suitable rod material, such as a wire with, for example, pairs of flats, be employed with the stapler of the invention. Such a square or other shaped wire lends itself to improved feeding characteristics minimizing jamming of the staples in the feeding track, and a square wire or wire with flats also exhibits other desirable features over round wire staples insofar as manufacture is concerned.

The operation of the skin stapler is best illustrated with reference to FIGS. 2-8. As seen therein, in operation, a row of staples 74, which are included with the skin stapler, are positioned atop driver 22 slidably mounted between the top and bottom covers 80 and 84 which are suitably secured together by extending elements 126 suitably crimped over notched out areas 128 of the top cover 80. The top and bottom covers 80 and 84 are fixed in place in the housing 12 by suitable means, such as the upwardly extension 130 which engages a slot 132 in the housing 12, and by a downwardly tip projection 134 of an arrowhead at the front of the housing 12 which arrowhead incidentally simply alerts the doctor or surgeon to point the nose of the stapler with the approximating blade 102 and the incision 140 at the point at which staples are to be placed. Slidably mounted above the driver 22 is a follower 72 which continually urges the row of staples against a conforming front underside surface of the escapement spring 76 (FIG. 8) or top housing cover, as best shown in FIG. 29. Attached to the bottom cover 84 is a resilient ejector 86 which is provided with a pair of upwardly projecting fingers 136 extending on both sides of the anvil 61. The ejector 86 is displaced downwardly out of the way when the trigger element 18 is pulled during crimping of a staple 74 by the elongated dimple 88 of the driver 22; and the fingers 136 lift a crimped stable 74 from the anvil 61 (FIGS. 7a-7b) when the trigger element 18 is released to return the stapler mechanism to its original start position. As only one staple is acted upon at one time during each cycle of operation, there is virtually no chance for the stapler of the invention to become jammed.

As the top cover 80 is provided with a rectangular opening partially covered by the escapement spring 76 and the housing 12 has a front window 138, the staples are visible to a doctor or surgeon thus giving an idea as to the number of staples 74 remaining in the stapler 10. As the stapler 10 does not employ replaceable staple cartridges, the entire stapler must be discarded and a new one used to complete a job. It is understood that even if only one or two staples are used for a suture, the stapler would still be discarded and not used again as such practice eliminates the problem of sterilization and contamination.

The start of a staple placement cycle generally commences when a single staple 74 is urged into position in front of the driver 22 the instant the driver 22 commences its retraction mode which is when the trigger element 18 is released and the actuating drum 24 pulls the driver 22 back. Thereafter, the driver 22 is advanced to commence bending the staple 74 around the anvil 61 and finally closing the staple 74, when the trigger element 18 is completely pulled in. Subsequently thereto, the trigger element 18 is released pulling back the driver 22, and the crimped staple 74 is lifted off the anvil 61 by means of the ejector's fingers 136, and a new cycle is commenced by the next staple urged into position in the same manner as experienced by the first staple. All of these sequences are clearly shown in FIGS. 4-7 in the various plan and sectional views taken generally along numerous section lines.

The ratchet mechanism is operative during each cycle or sequence of staple placement or operation as it precludes double-loading and ensures at all times that only one staple is being acted upon during any one cycle of operation. Thus, such a mechanism aids in preventing jamming as once a cycle is started, it must be completed before a new cycle is commenced. The toothed elements of each ratchet mechanism disclosed herein thus engage the pawl arm to stop the stapler from being recycled in "mid-stream" before a full cycle of operation is made with the trigger.

Another feature of the present invention is the curved shape of the top portion of the housing or frame structure. This curved section and nose portion at the distal end thereof greatly increases visibility at the work site as the stapler does not block the surgeon's line of sight during use of the instrument.

It should also be appreciated that the follower is preferably made of a low friction material to facilitate movement of same between the driver and the top cover, while the elements of the housing other than the follower including top and bottom covers, ejector, driver and release member or escapement spring are all of a suitable metal, such as stainless steel.

The handle or frame portion including the trigger element may comprise an injection molded plastic material which is capable of sterilization as an assembled unit and is subject to complete sterilization once the staples are stacked in the stapler or housing and all parts of the stapler are secured together.

Although the present invention has been described in some detail by way of illustration and example for purposes of clarity and understanding, it will, of course, be understood that various changes and modifications may be made in the form, details, and arrangements of the parts without departing from the scope of the invention as set forth in the following claims.

What is claimed is:

1. A surgical stapler adapted to be hand held, having a staple supply for suturing tissue with a plurality of staples and having a frame structure with a curved nose section, comprising:

an anvil, a housing structure having a single track therein and having a curved nose section shaped like said curved nose section of said frame structure for a driver-follower assembly unit; the follower being secured to the driver and travelling in a slot provided in the driver and being resiliently biased so as to continuously urge said plurality of staples, which are visible through a top front window in said stapler, and which are stacked end to end atop said driver to a forwardly position, a release member disposed above the most forward staple for uring said staple into position in front of said driver; said driver being manually actuated by actuating means for cyclically travelling between a forming position for closing said staple about said anvil and a retracting position in said track, for reloading a next staple in front of said driver, and said actuating means including a toggle-like drive mechanism providing an increasing force to said driver for forming said staple about said anvil, whereby the nose section of said staples having said window provides a visual indication of the staple supply.

2. The surgical stapler according to claim 1, wherein said housing structure incorporates said anvil and is encompassed within said frame structure having said curved nose section and a depending handle portion with a translatable trigger element connected to said actuating means.

3. The surgical stapler according to claim 1, wherein said housing structure comprises top and bottom covers secured together and forming said single track therebetween; and said top cover having an aperture coincident with aperture means in the curved nose section of said frame structure for enabling said staple supply to be visible at all times, thus alerting a doctor when said staple supply is about to be exhausted.

4. The surgical stapler according to claim 3, wherein said bottom cover and said driver are provided with mutually cooperative associated elements for providing alignment of said driver in said track, thereby ensuring the centering of said staple about said anvil.

5. The surgical stapler according to claim 4, wherein said cooperatively associated elements include pin means and mating groove means provided on said bottom cover and said driver.

6. The surgical stapler according to claim 4, wherein said bottom cover includes a tongue-like element extending out of the plane of said bottom cover, and said driver includes a mating groove engaged with said tongue-like element for facilitating the formation of an equal box-like staple upon the bending of said staple about said anvil.

7. The surgical stapler according to claim 4, including latching means for precluding said trigger element from releasing with substantially full retracted force in the event one's grip about said stapler slips or is accidentally jarred.

8. The surgical stapler according to claim 7, including an ejector secured to said bottom cover having a pair of cantilevered legs which urge each staple formed by said driver off sid anvil upon retraction of said driver.

9. The surgical stapler according to claim 8, wherein said release member employs a three point contact with each staple for urging one staple at a time in front of said driver during each cycle of operation of said stapler.

* * * * *